(12) United States Patent
Wall et al.

(10) Patent No.: US 11,730,546 B2
(45) Date of Patent: Aug. 22, 2023

(54) SPINAL IMPLANT SYSTEM AND METHOD

(71) Applicant: Warsaw Orthopedic, Inc., Warsaw, IN (US)

(72) Inventors: Daniel Paxton Wall, Cordova, TN (US); Christopher Good, Great Falls, VA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 611 days.

(21) Appl. No.: 16/752,557

(22) Filed: Jan. 24, 2020

(65) Prior Publication Data

US 2021/0228280 A1 Jul. 29, 2021

(51) Int. Cl.
*A61B 34/20* (2016.01)
*A61B 17/70* (2006.01)
*A61M 29/00* (2006.01)
*A61B 17/17* (2006.01)
*A61B 17/34* (2006.01)
(Continued)

(52) U.S. Cl.
CPC .......... *A61B 34/20* (2016.02); *A61B 17/1757* (2013.01); *A61B 17/7076* (2013.01); *A61M 29/00* (2013.01); *A61B 17/3421* (2013.01); *A61B 34/30* (2016.02); *A61B 2017/0088* (2013.01); *A61B 2017/00867* (2013.01); *A61B 2017/00933* (2013.01); *A61B 2017/3454* (2013.01); *A61B 2034/2051* (2016.02); *A61B 2090/376* (2016.02);
(Continued)

(58) Field of Classification Search
CPC ..... A61B 34/20; A61B 17/17; A61B 17/1757; A61B 17/70; A61B 17/7076; A61M 29/00
See application file for complete search history.

(56) References Cited

U.S. PATENT DOCUMENTS

2008/0045970 A1\* 2/2008 Saidha ............... A61B 17/7035
81/436
2016/0166338 A1\* 6/2016 Hartmann .......... A61B 17/1703
606/130

(Continued)

OTHER PUBLICATIONS

International Search Report, ISA: Korean Intellectual Property Office 189 Cheongsa-ro, Seo-gu, Daejeon 35208, Republic of Korea, dated May 18, 2021, International application No. PCT/US2021/014619.

(Continued)

*Primary Examiner* — Christopher J Beccia
(74) *Attorney, Agent, or Firm* — Sorell, Lenna & Schmidt, LLP

(57) ABSTRACT

A surgical instrument comprises a first member extending between a proximal end and a distal end configured for fixation with tissue. A second member defines a longitudinal passageway and is connected with a navigation component such that the distal end is disposable with the passageway at a selected distance from the navigation component. The navigation component is positioned relative to a sensor to communicate a signal representative of an orientation of the first member. A third member extends between a proximal end and a distal end. The third member is mountable with the first member along the orientation such that the distal end of the third member is engageable with the tissue. Systems, spinal implants, constructs and methods are disclosed.

20 Claims, 12 Drawing Sheets

(51) Int. Cl.
 *A61B 17/00* (2006.01)
 *A61B 90/00* (2016.01)
 *A61B 34/30* (2016.01)

(52) U.S. Cl.
 CPC .............. *A61B 2090/3762* (2016.02); *A61B 2090/3764* (2016.02); *A61B 2090/3966* (2016.02)

(56) References Cited

U.S. PATENT DOCUMENTS

| | | |
|---|---|---|
| 2016/0220320 A1 | 8/2016 | Crawford et al. |
| 2017/0333057 A1* | 11/2017 | Kostrzewski ...... A61B 17/3417 |
| 2018/0116814 A1 | 5/2018 | Sullivan et al. |
| 2018/0199951 A1 | 7/2018 | Chappuis et al. |

OTHER PUBLICATIONS

Written Opinion of the International Searching Authority, Korean Intellectual Property Office 189 Cheongsa-ro, Seo-gu, Daejeon 35208, Republic of Korea, dated May 18, 2021, International application No. PCT/US2021/014619.

\* cited by examiner

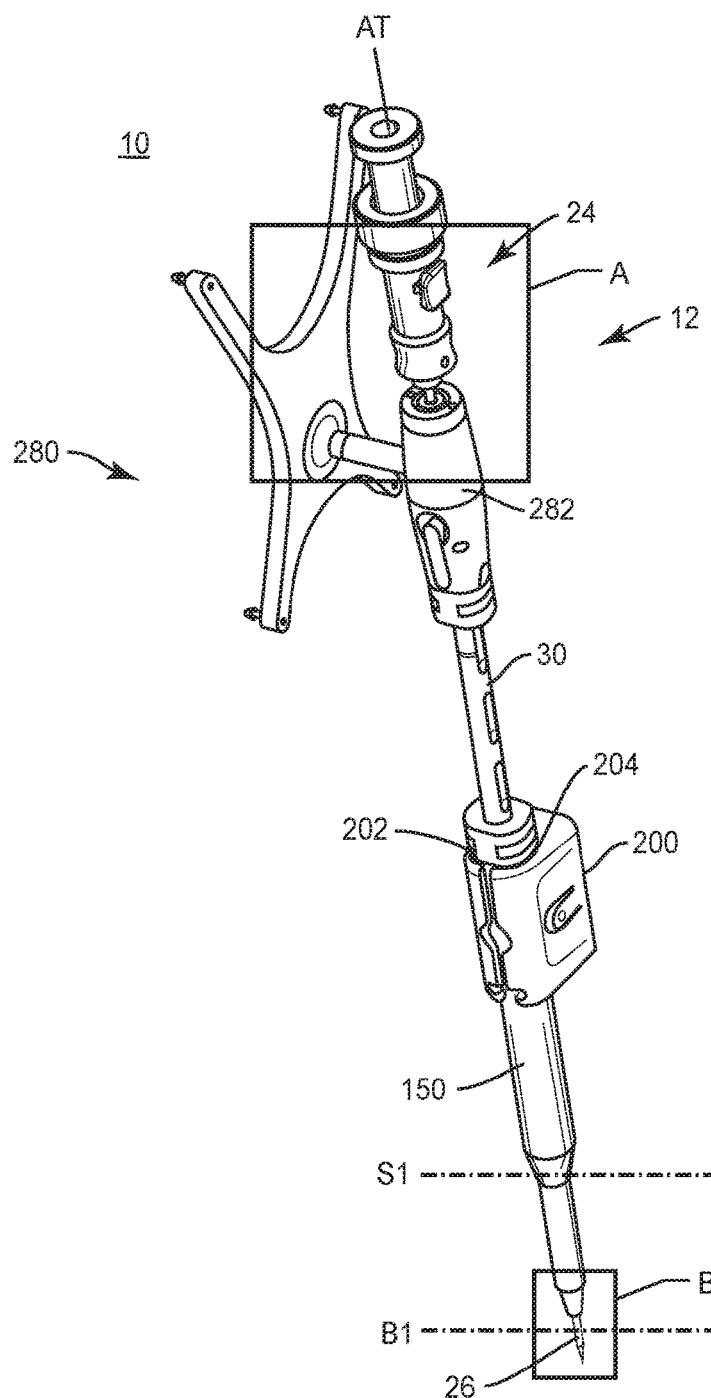
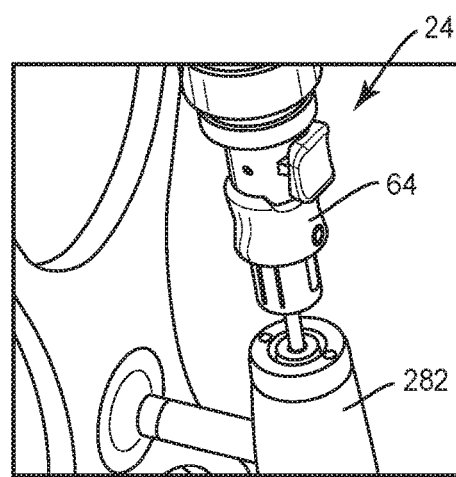
FIG. 15
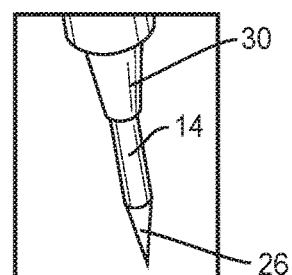
FIG. 16
FIG. 14

SPINAL IMPLANT SYSTEM AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises a first member extending between a proximal end and a distal end configured for fixation with tissue. A second member defines a longitudinal passageway and is connected with a navigation component such that the distal end is disposable with the passageway at a selected distance from the navigation component. The navigation component is positioned relative to a sensor to communicate a signal representative of an orientation of the first member. A third member extends between a proximal end and a distal end. The third member is mountable with the first member along the orientation such that the distal end of the third member is engageable with the tissue. In some embodiments, systems, spinal implants, constructs and methods are disclosed.

In one embodiment, the surgical instrument includes an anchor extending between a proximal end and a distal end configured for fixation with tissue. A dilator defines a longitudinal passageway and is connected with a navigation component such that the distal end is disposable with the passageway at a selected distance from the navigation component. The navigation component is positioned relative to a sensor to communicate a signal representative of an orientation of the anchor. A drill guide is mountable with the anchor along the orientation such that a distal end of the drill guide is engageable with the tissue.

In one embodiment, the surgical instrument includes an anchor configured for fixation with tissue. A dilator defines a longitudinal passageway and is connected with a navigation component such that the distal end is disposable with the passageway at a selected distance from the navigation component. The navigation component is positioned relative to a sensor to communicate a signal representative of an orientation of the anchor. A drill guide is mountable with the anchor along the orientation such that a distal end of the drill guide is engageable with the tissue. An anchor tool is connectable with the anchor and configured to adjust a depth of the anchor relative to tissue and the navigation component.

BRIEF DESCRIPTION OF THE DRAWINGS

The present disclosure will become more readily apparent from the specific description accompanied by the following drawings, in which:

FIG. 14 is a perspective view of components of one embodiment of a surgical system in accordance with the principles of the present disclosure;

FIG. 15 is a perspective view of detail A shown in FIG. 14;

FIG. 16 is a perspective view of detail B shown in FIG. 14;

DETAILED DESCRIPTION

Figure 1:
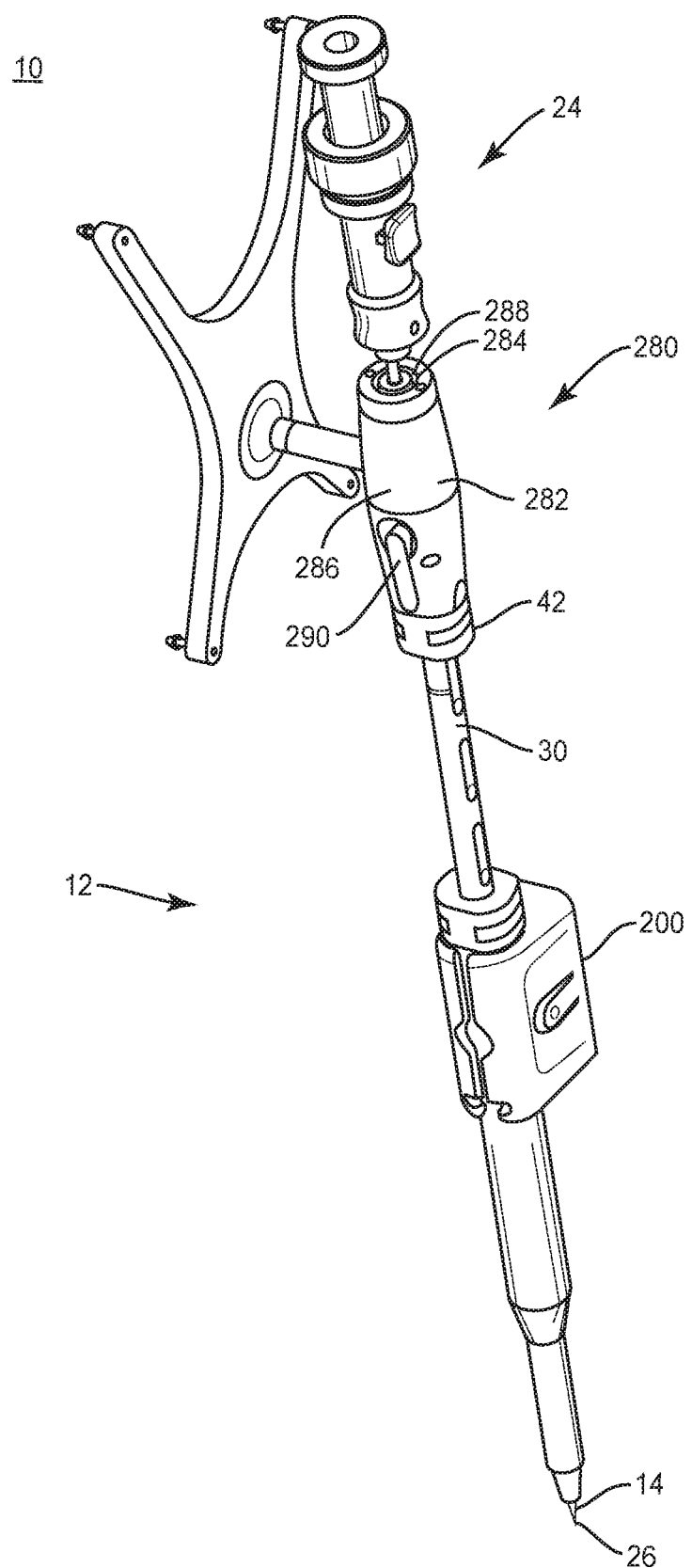
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument including an anchor and a dilator configured for engagement with bone utilizing navigation. In some embodiments, the surgical instrument is configured to guide a drill guide along the anchor to facilitate engagement of the drill guide with bone. In some embodiments, the surgical system includes a navigated cannulated dilator, an anchor and an anchor tool. In some embodiments, the anchor is disposed with the dilator and engaged with bone. In some embodiments, the anchor is tamped into bone and the dilator is removed. In some embodiments, the anchor is engaged with bone utilizing navigation. In some embodiments, a drill guide is guided over the anchor and tamped into bone. In some embodiments, the anchor is removable.

In some embodiments, the present surgical system comprises a surgical instrument including the anchor and the dilator being configured to confirm a trajectory when tamping the drill guide. In some embodiments, the drill guide is engaged with bone utilizing navigation. In some embodiments, the anchor is disposed with the dilator and the dilator is connected with a navigation component.

In some embodiments, the present surgical system comprises a surgical instrument including a disposable anchor. In some embodiments, the anchor includes a groove disposed at a proximal end. In some embodiments, the present surgical system comprises an anchor tool having a depressible button to connect and lock the anchor with the anchor tool. In some embodiments, the anchor tool includes a depth setting device.

In some embodiments, the present surgical system comprises a surgical instrument including a navigation component that is connected with the dilator and the anchor is inserted through the dilator. In some embodiments, a distal tip of the anchor extends beyond a distal end of the dilator. In some embodiments, the distal tip extends a distance from the dilator. In some embodiments, the distance the distal tip extends is equal to a length programmed into the navigation system and is utilized to calculate depth navigation. In some embodiments, the depth setting device maintains extension of the distal tip from the dilator.

In some embodiments, the present surgical system includes a method of treating a spine including the step of inserting the surgical instrument through a cannula to a surgical site. In some embodiments, the method includes the step of driving or malleting the anchor tool to provisionally engage the distal tip of the anchor into bone. In some embodiments, the method includes the step of translating the depth setting device to a retracted position to allow for driving the anchor deeper once the trajectory has been set and then malleting the anchor to a selected depth. In some embodiments, the method includes the step of actuating the button to disengage the anchor tool from the anchor and removing the dilator. In some embodiments, the method includes the steps of mounting a drill guide over the anchor and malleting the drill guide into bone. In some embodiments, the method includes the step of reconnecting the anchor tool with the anchor and using a slap hammer to remove the anchor from bone. In some embodiments, a drill is disposed with the drill guide and utilized to implant spinal implants. See, for example, the embodiments and disclosure of systems and methods of engaging one or more surgical instruments with bone utilizing surgical navigation, shown and described in commonly owned and assigned U.S. patent application Ser. No. 16/752,565 filed Jan. 24, 2020, and published as U.S. Patent Application Publication No. US 2021-0228244 A1, on Jul. 29, 2021, now U.S. Pat. No. 11,612,419, issued Mar. 28, 2023, the entire contents of which being incorporated herein by reference.

In some embodiments, the present surgical system comprises a surgical instrument including a straight anchor having a pointed distal tip. In some embodiments, the anchor includes a groove at the proximal end to facilitate connection with the anchor tool. In some embodiments, the surgical instrument includes a cannulated dilator. In some embodiments, the dilator includes a tapered distal tip. In some embodiments, the dilator includes a passageway formed by slots milled from each side along the dilator.

In some embodiments, the present surgical system comprises a surgical instrument including an anchor tool having a depth setting device, an anchor retention button and a slap hammer. In some embodiments, the depth setting device is disposable in a fully extended position to set the depth of the anchor for navigation. In some embodiments, pins connect the depth setting device with the anchor tool in a keyed configuration. In some embodiments, the button is biased outwards by a spring. In some embodiments, the button is engageable with the groove on the anchor to fix the anchor tool with the anchor. In some embodiments, the slap hammer is moveable to facilitate removing the anchor from bone.

In some embodiments, the present surgical system comprises a surgical instrument including a depth setting device being moveable between a retracted position and an extended position. In some embodiments, in the retracted position, a spring tab locks the depth setting device. In some embodiments, the anchor tool includes pins to retain the button with a body of the anchor tool. In some embodiments, a flange is welded with the anchor tool after the slap hammer is assembled. In some embodiments, a proximal end of the anchor tool is hollow to reduce a weight of the anchor tool.

In some embodiments, the present system is employed with a method used with surgical navigation, for example, fluoroscope or image guidance. In some embodiments, the presently disclosed system and/or method reduce operating time for a surgical procedure and reduce radiation exposure due to fluoroscope or image guidance, for example, by eliminating procedural steps and patient repositioning by implanting system components in one body position.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-12, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 22:
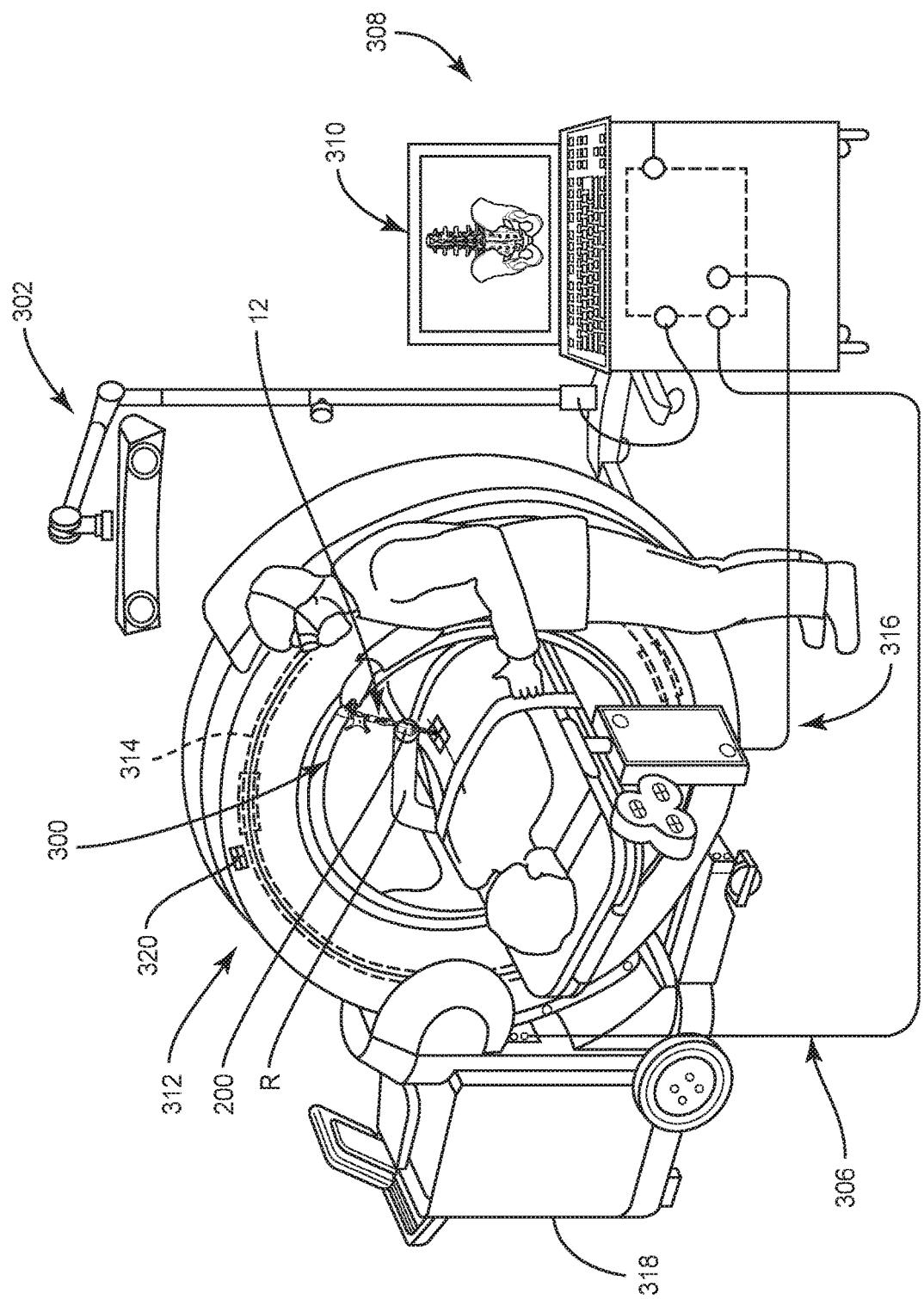
FIG. 22 is a perspective view of components of one embodiment of a surgical system in accordance with the principles of the present disclosure.

Spinal implant system 10 includes a surgical instrument 12. Surgical instrument 12 can be employed with an end effector 200, as shown in FIG. 1, to facilitate implantation with a robotic arm R (FIG. 22). Surgical instrument 12 is guided through end effector 200 for guide-wireless insertion of a spinal implant, for example, a bone fastener 100, as described herein.

Figure 2:
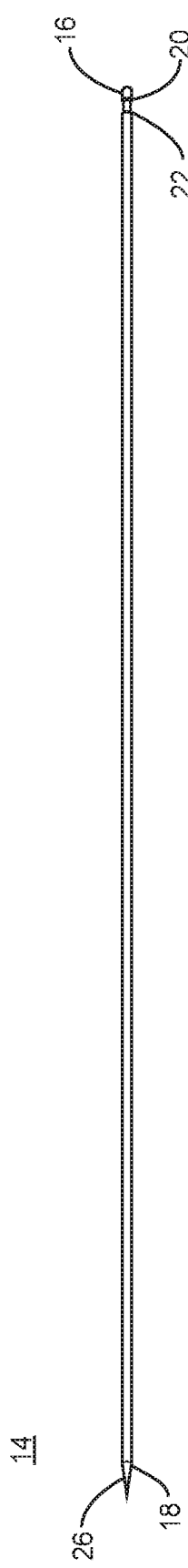
FIG. 2 is a perspective view of components of the surgical system shown in FIG. 1.

Surgical instrument 12 includes a member, for example, an anchor 14. Anchor 14 extends between a proximal end 16 and a distal end 18, as shown in FIG. 2. Proximal end 16 includes a surface 20 that defines a groove 22. In some embodiments, groove 22 is disposed circumferentially about end 16. Groove 22 is configured for disposal of a portion of a member, for example, an anchor tool 24 to releasably fix anchor tool 24 with anchor 14, as described herein.

End 18 includes a tip 26. In some embodiments, tip 26 is pointed or sharpened to facilitate penetration of tissue. In some embodiments, end 18 may have various surface configurations, for example, smooth, rough, arcuate, undulating, porous, semi-porous, dimpled, polished and/or textured. Tip 26 is configured to fix anchor 14 with tissue to provide an orientation, for example, an axial trajectory for the components of surgical instrument 12, as described herein.

Figure 3:
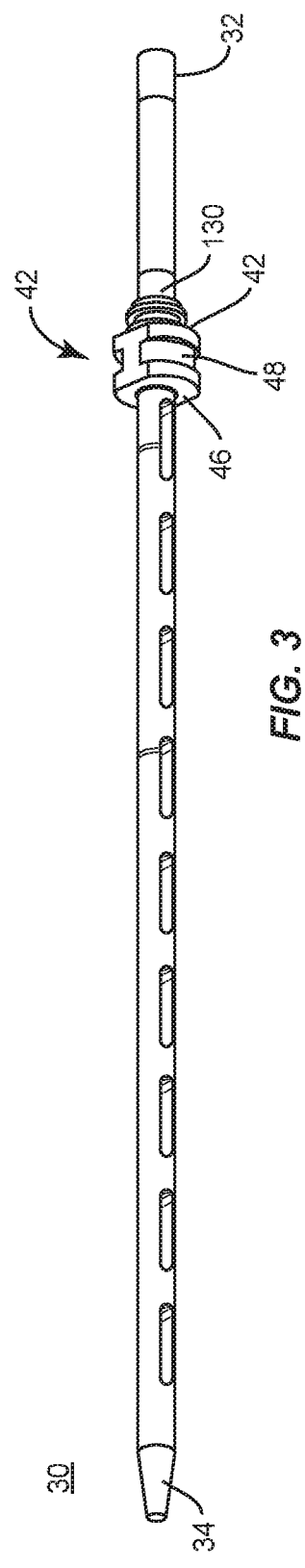
FIG. 3 is a perspective view of components of the surgical system shown in FIG. 1.
Figure 4:
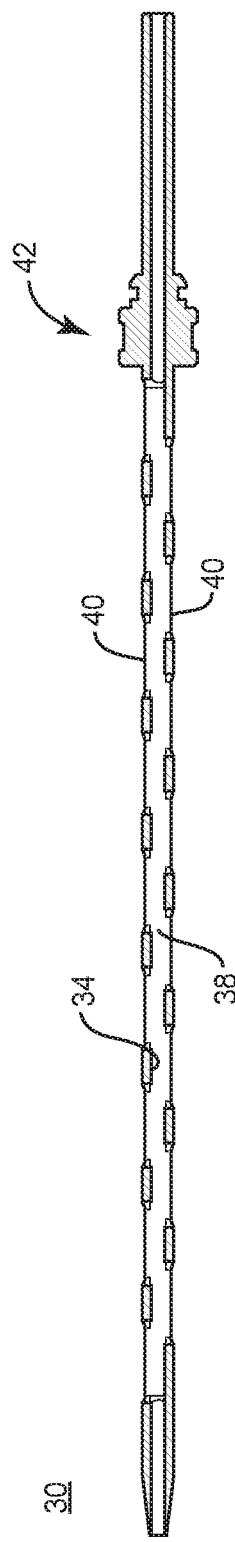
FIG. 4 is a cross section view of the components shown in FIG. 3.
Figure 5:
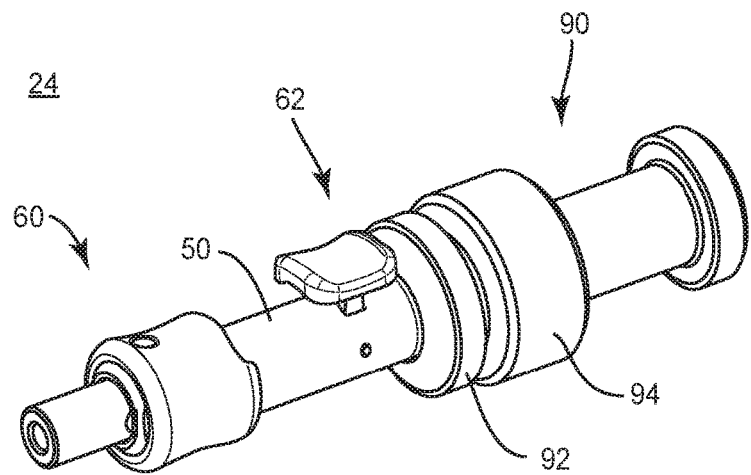
FIG. 5 is a perspective view of components of the surgical system shown in FIG. 1.

Surgical instrument 12 includes a member, for example, a dilator 30, as shown in FIGS. 3 and 4. Dilator 30 extends between a proximal end 32 and a distal end 34. Dilator 30 defines a longitudinal axis X1. In some embodiments, dilator 30 may have various configurations including, for example, round, oval, polygonal, irregular, consistent, variable, uniform and non-uniform. Dilator 30 includes a surface 36 that defines a longitudinal passageway 38 extending between ends 32, 34. In some embodiments, passageway 38 is manufactured by milling overlapping slots 40 through surface 36 along dilator 30, as shown in FIG. 4.

End 34 includes a tapered configuration to facilitate spacing of tissue. In some embodiments, end 34 may have various cross section configurations, such as, for example, oval, oblong, triangular, rectangular, square, polygonal, irregular, uniform, non-uniform, variable and/or tubular.

Dilator 30 includes a mating element, for example, a bushing 42. Bushing 42 is configured to connect a navigation component 280 with surgical instrument 12. Bushing 42 includes a flange 44 and a flange 46 that is spaced apart from flange 44. Bushing 42 includes a recess 48 between flanges 44, 46. Bushing 42 is disposed with dilator 30. Dilator 30 includes mating surfaces, for example, datum surfaces 130. Surface 130 is disposed on shaft dilator 30 at a selected distance from distal end 34. Surface 130 is detectable by image guidance and utilized to determine a position of navigation component 280, as described herein, and/or surgical instrument 12 during a surgical procedure. Surface 130 is configured for connection with a portion of navigation component 280 to facilitate positioning and/or tracking of navigation component 280 and/or surgical instrument 12 during a surgical procedure. In some embodiments, dilator 30 may include one or a plurality of mating surfaces, as described herein.

Navigation component 280, as shown in FIG. 1, includes a collar 282 having an inner surface 284 and an outer surface 286. Surface 284 defines a passageway 288. Surface 284 is configured for releasable engagement with bushing 250. Passageway 288 is configured to receive dilator 30 and a portion of bushing 42. Collar 282 includes a lock, for example, a resilient prong or tab 290. Navigation component 280 is connected with bushing 42 by tab 290. In some embodiments, collar 282 may include one or a plurality of locks, as described herein.

Passageway 38 is configured for disposal of anchor 14, as described herein. Dilator 30 is removably mounted with anchor 14 such that tip 26 is positioned at a selected distance from navigation component 280. Navigation component 280 is positioned relative to a sensor to communicate a signal representative of the orientation of anchor 14 during engagement with tissue. Tip 26 is configured to fix anchor 14 with tissue to provide the axial trajectory for the components of surgical instrument 12, as described herein.

Figure 6:
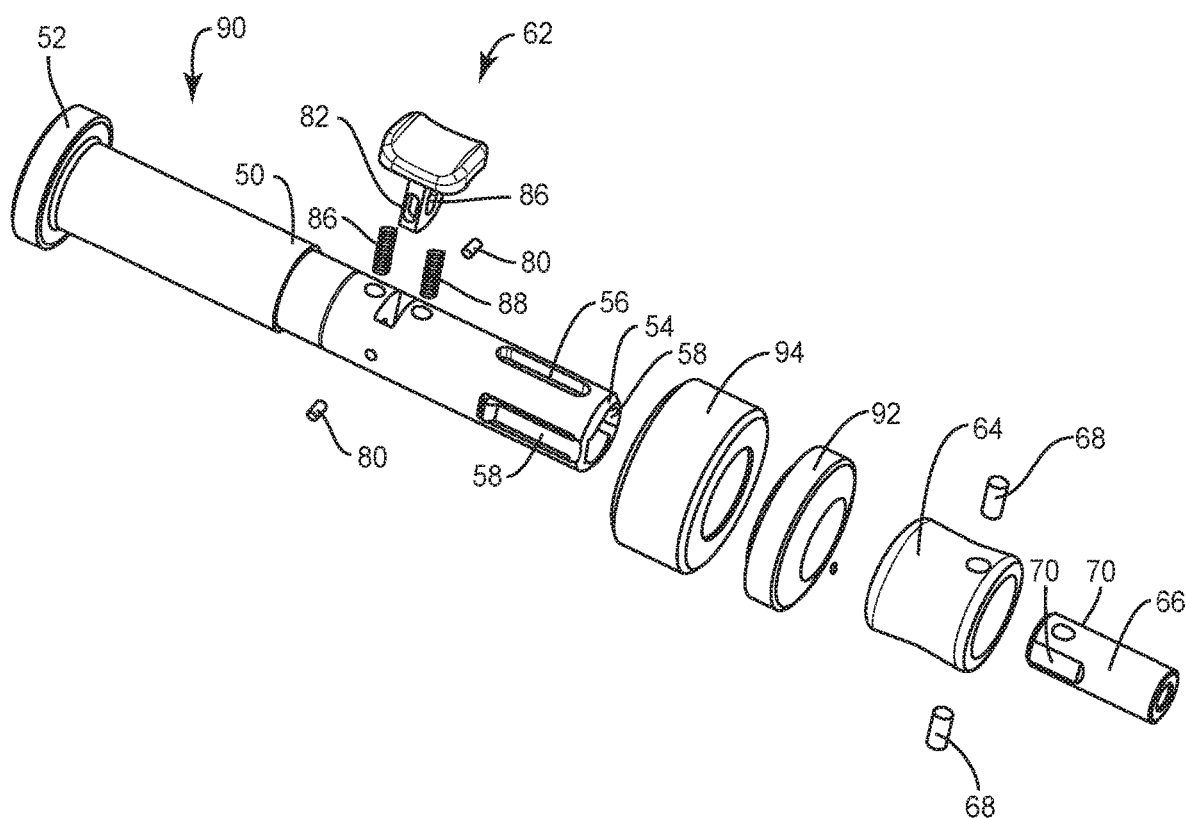
FIG. 6 is a perspective view of the components shown in FIG. 5 with parts separated.

Anchor tool 24 includes a body 50. Body 50 extends between an end 52 and an end 54. End 54 includes slots 56 and spring tabs 58, as shown in FIG. 6. Anchor tool 24 includes a part, for example, a depth setter 60 and a button 62, as shown in FIGS. 5-9.

Figure 7:
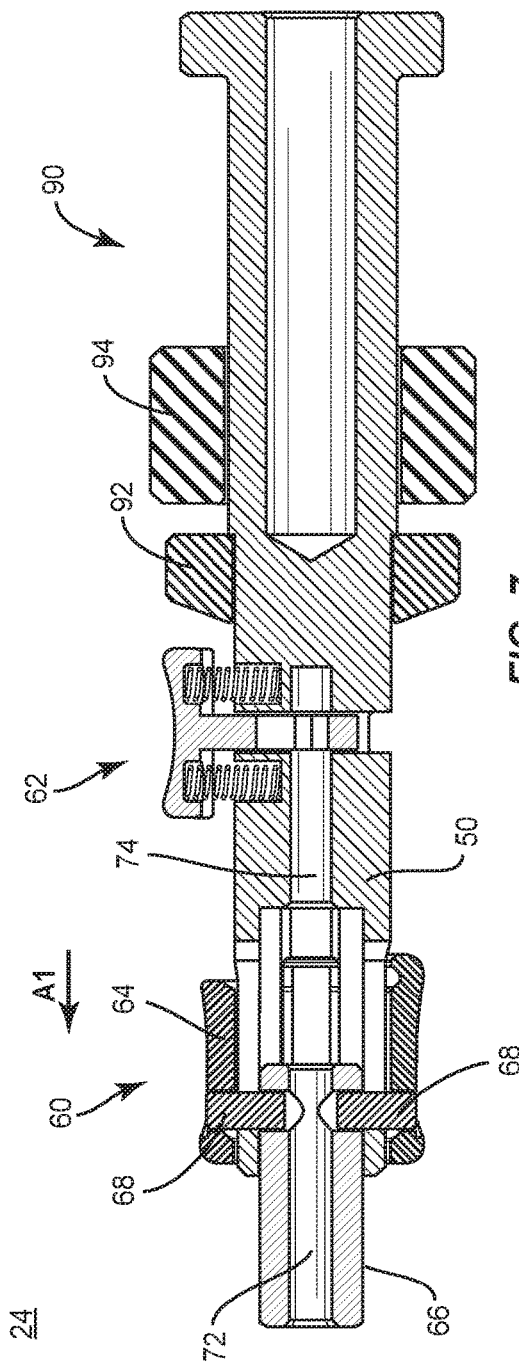
FIG. 7 is a cross section view of the components shown in FIG. 5.
Figure 8:
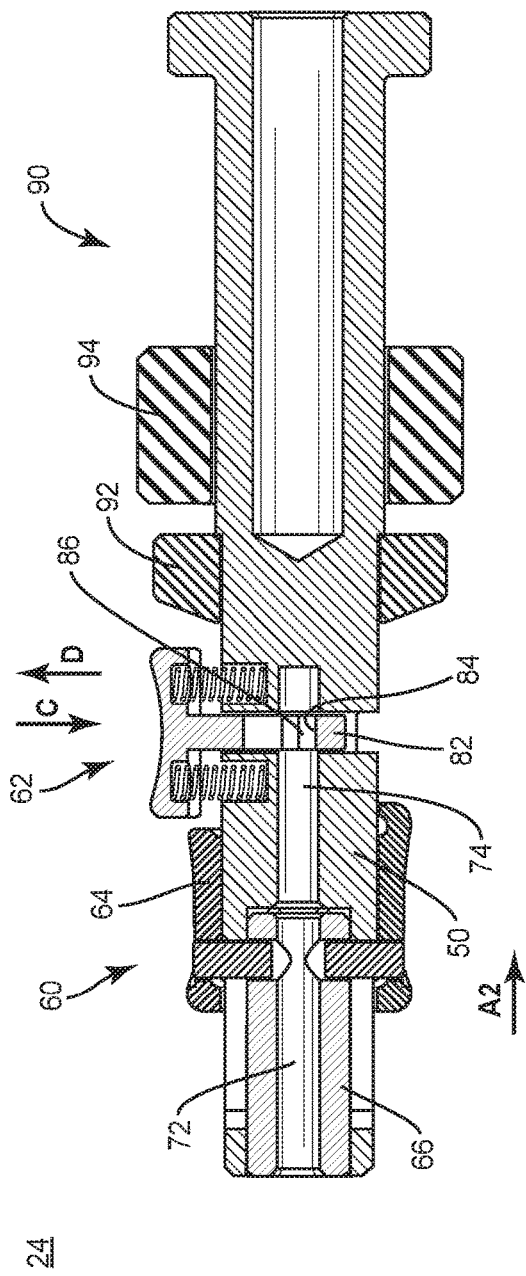
FIG. 8 is a cross section view of the components shown in FIG. 5.
Figure 9:
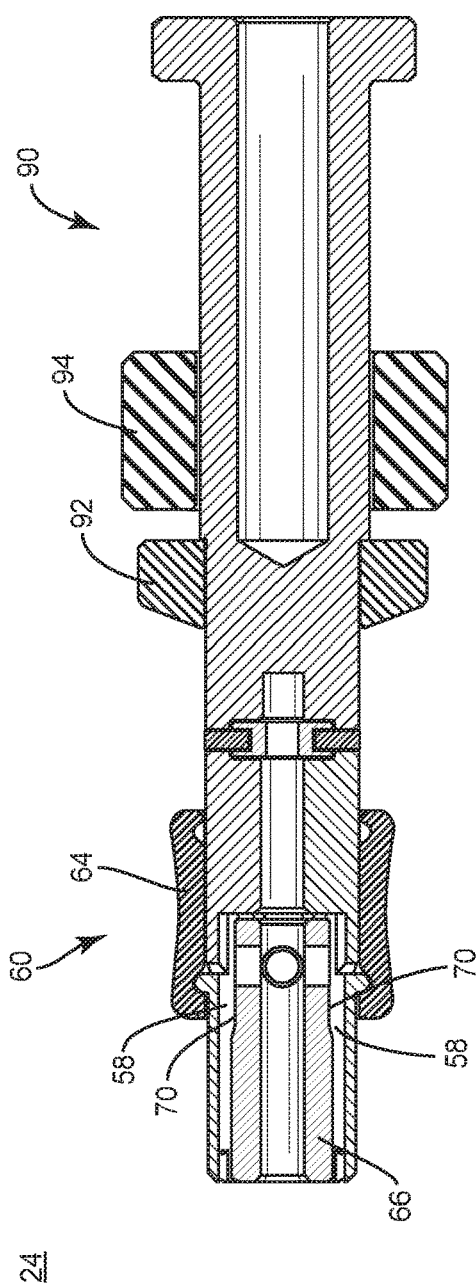
FIG. 9 is a cross section view of the components shown in FIG. 5.
Figure 10:
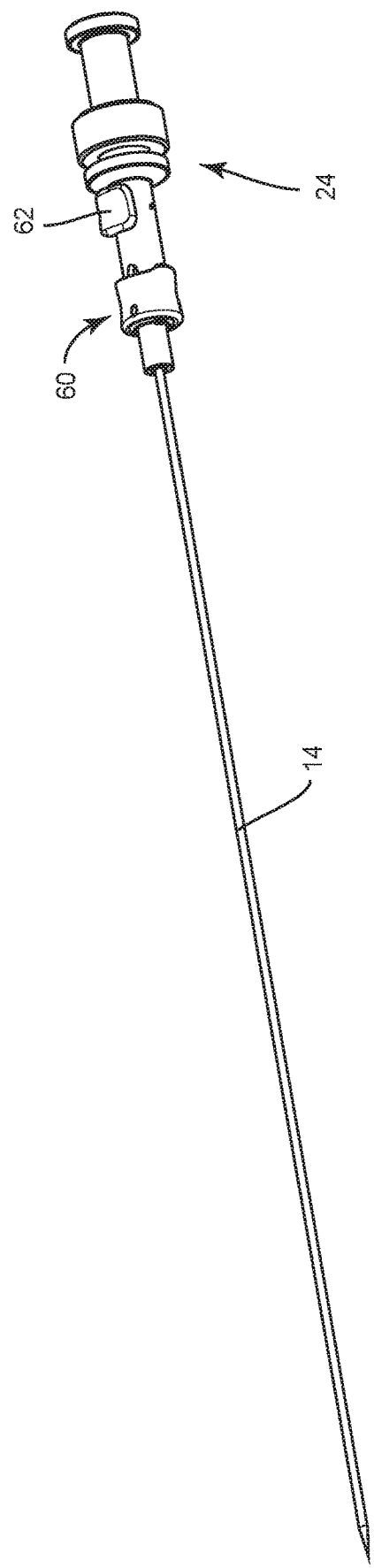
FIG. 10 is a perspective view of components of the surgical system shown in FIG. 1.
Figure 11:
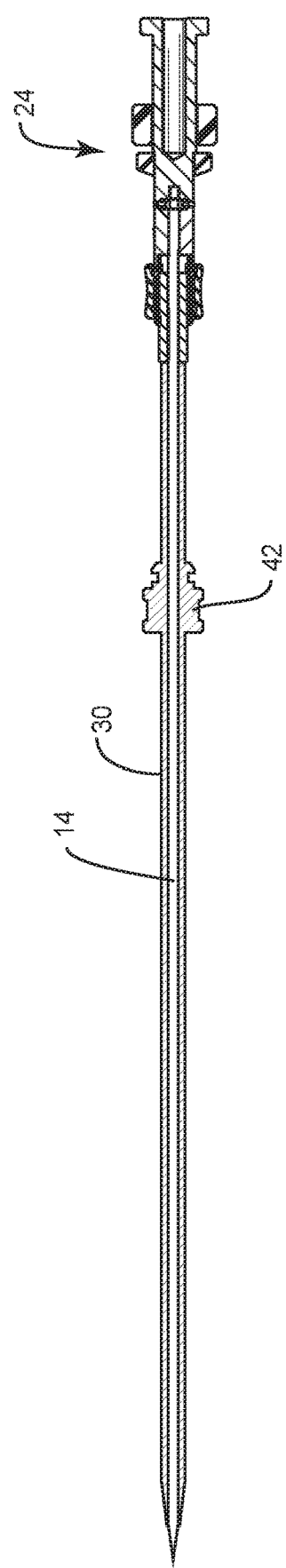
FIG. 11 is a cross section view of components of the surgical system shown in FIG. 1.
Figure 12:
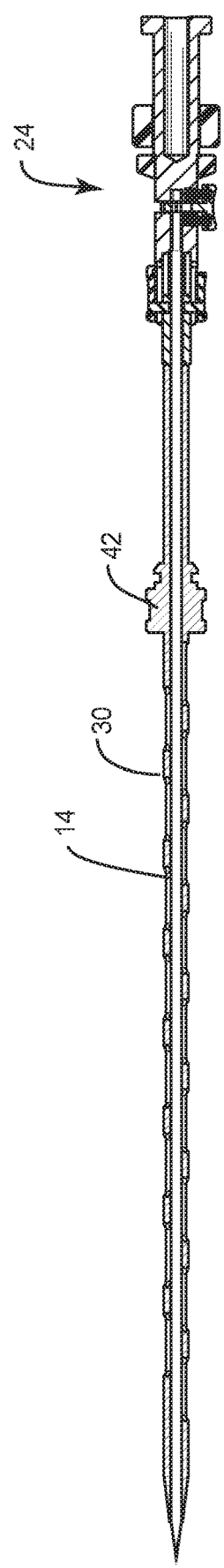
FIG. 12 is a cross section view of components of the surgical system shown in FIG. 1.

Depth setter 60 includes a slider 64 and a sleeve 66. Sleeve 66 includes a surface 70 configured for engagement with spring tabs 58 in a friction fit configuration to fix sleeve 66 in the extended position, as shown in FIG. 7 and/or the retracted position, as shown in FIG. 8. In some embodiments, sleeve 66 and body 50 may be disposed with an integral connection, friction fit, pressure fit, interlocking engagement, mating engagement, dovetail connection, clips, barbs, tongue in groove, threaded, magnetic and/or key/keyslot. Sleeve 66 includes a surface that defines a channel 72. Channel 72 is disposed in communication with a channel 74 of body 50, as shown in FIG. 7. Channels 72, 74 are configured for disposal of anchor 14, as described herein.

Pins 68 extend through slots 56 to connect slider 64 and sleeve 66 with body 50, as shown in FIGS. 7 and 8, such that translation of slider 64 causes translation of sleeve 66 between an extended position and a retracted position relative to body 50.

Figure 13:
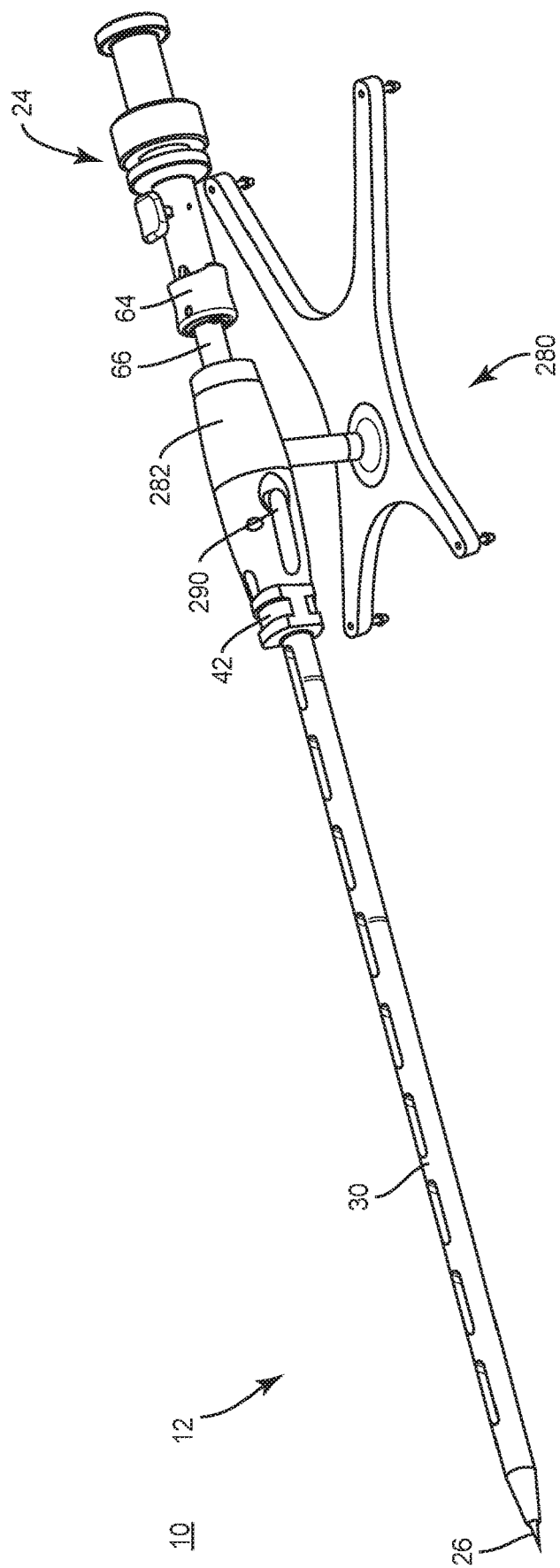
FIG. 13 is a perspective view of components of one embodiment of a surgical system with parts separated in accordance with the principles of the present disclosure.

For example, translation of slider 64, in a direction shown by arrow A1 in FIG. 7, causes sleeve 66 to simultaneously translate via connection of pins 68, in a direction shown by arrow A1 in FIG. 7, to the extended position. In the extended position, sleeve 66 is disposed in an abutting engagement with collar 282 of navigation component 280, as shown in FIG. 13. In the extended position, sleeve 66 positions the extension and/or depth of tip 26 beyond end 34 a selected distance from navigation component 280. Sleeve 66 resists and/or prevents extension of tip 26 further than the selected distance. Tip 26 is provisionally fixed with tissue under navigation by communication of navigation component 280 with a surgical navigation system 306, as described herein.

Translation of slider 64 in the opposite direction, in a direction shown by arrow A2 in FIG. 8, causes sleeve 66 to simultaneously translate, in the direction shown by arrow A2 in FIG. 8, to the retracted position. In the retracted position, sleeve 66 is spaced a distance from collar 282, as shown in FIG. 15, to allow anchor 14 to translate through dilator 30 to extend further from end 34 of dilator 30 to facilitate driving anchor 14 a further depth into tissue for docking.

Button 62 is connected with body 50 by pins 80. Button 62 includes a protrusion 82 having a surface 84 that defines an opening 86. Opening 86 is configured for disposal of anchor 14 and surface 84 is configured to engage groove 22 to fix anchor 14 with anchor tool 24. Button 62 is biased to a closed position by springs 88 such that protrusion 82 blocks channel 74. To capture anchor 14, a force is applied to button 62, in a direction shown by arrow C in FIG. 8, causing opening 86 to align with channel 74 to allow anchor 14 to translate therethrough. Button 62 is released and the bias of springs 88 pushes button 62, in a direction shown by arrow D in FIG. 8, causing surface 84 to engage surface 20 of groove 22 to capture anchor 14. To release anchor 14, a force is applied to button 62, in the direction shown by arrow C in FIG. 8, causing surface 84 to disengage surface 20 of groove 22 to release anchor 14. Opening 86 aligns with channel 74 to allow anchor 14 to translate therethrough for disengagement from anchor tool 24.

In some embodiments, anchor tool 24 includes a handle portion 90 that includes a flange 92, a slap hammer 94 and an end flange 96. Slap hammer 94 translates between flange 92 and end flange 96 to facilitate removing anchor 14 from the surgical site. In some embodiments, handle portion 90 is hollow to reduce the weight of anchor tool 24.

Figure 20:
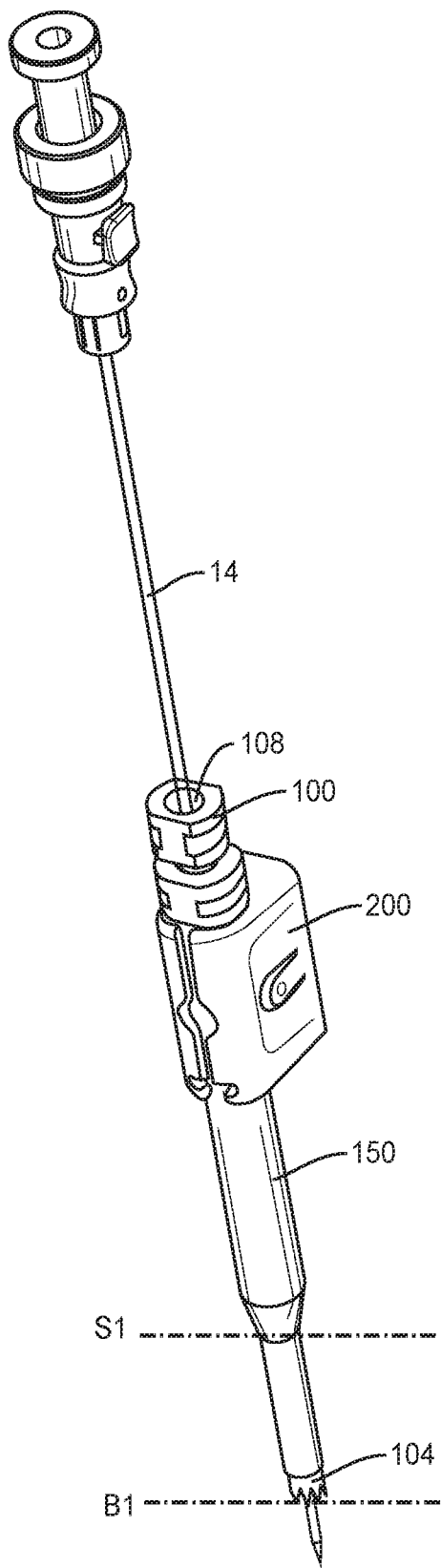
FIG. 20 is a perspective view of components of one embodiment of a surgical system in accordance with the principles of the present disclosure.
Figure 21:
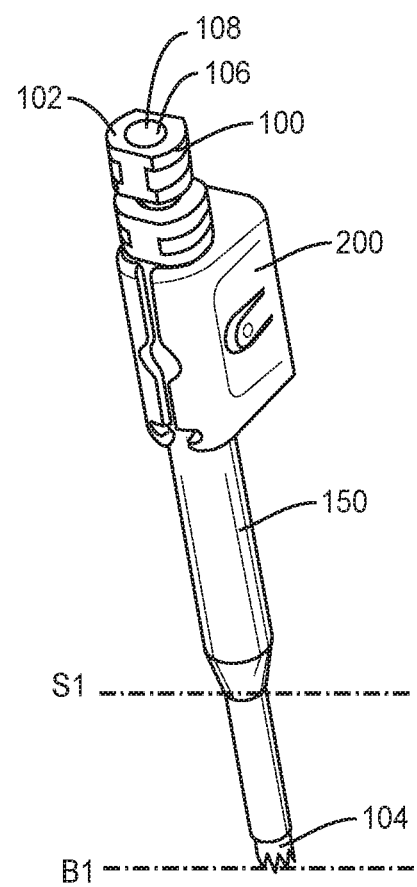
FIG. 21 is a perspective view of components of one embodiment of a surgical system in accordance with the principles of the present disclosure.

Surgical instrument 12 includes a member, for example, a drill guide 100, as shown in FIGS. 20 and 21. Drill guide 100 extends between a proximal end 102 and a distal end 104. Distal end 104 is configured to engage tissue. Drill guide 100 includes a surface 106 that defines a passageway 108 configured for disposal of a drill. Drill guide 100 is utilized to assist in control and guidance of a surgical drill. Drill guide 100 is securely docked by mounting drill guide 100 with anchor 14. Anchor 14 guides drill guide 100 along the axial trajectory to engage distal end 104 of drill guide 100 with bone.

In assembly, operation and use, as shown in FIGS. 13-22, spinal implant system 10, similar to the systems and methods described herein, is employed with a surgical procedure, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In some embodiments, a scalpel (not shown) is oriented for disposal with end effector 200 of robotic arm R, as described herein. An incision is made in the skin 51 of a patient with the scalpel, which creates a surgical pathway for implantation of components of spinal implant system 10. A speculum (not shown) can be employed to assist in creating the surgical pathway. A preparation instrument (not shown) can be employed to prepare tissue surfaces as well as for aspiration and irrigation of a surgical region. A cannula 150 is inserted into end effector 200 and is inserted into the surgical pathway. Surgical instrument 12 is assembled. Anchor 14 is disposed with passageway 38 of dilator 30. Navigation component 280 is connected with dilator 30. Navigation component 280 is translated along dilator 30 into a mating engagement with surface 130 and connected with bushing 42 by tab 290.

Anchor tool 24 is connected with anchor 14. Anchor 14 is translated into channel 72 and channel 74. Button 62 is actuated causing opening 86 to align with channel 74 to allow anchor 14 to translate therethrough. Button 62 is released and the bias of springs 88 pushes button 62 causing surface 84 to engage surface 20 of groove 22 to capture anchor 14.

Slider 64 is translated and causes sleeve 66 to simultaneously translate via connection of pins 68 into the extended position. In the extended position, sleeve 66 is disposed in an abutting engagement with collar 282 of navigation component 280, as shown in FIG. 13. In the extended position, sleeve 66 positions the extension and/or depth of tip 26 beyond end 34 a selected distance from navigation component 280 and surface 130. Sleeve 66 resists and/or prevents extension of tip 26 further than the selected distance.

Surgical instrument 12 is inserted into cannula 150. Dilator 30 expands skin 51 along the surgical pathway. Navigation component 280 is oriented relative to a sensor array 302, as shown in FIG. 22, to facilitate communication between navigation component 280 and sensor array 302 during a surgical procedure, as described herein.

Navigation component 280 is configured to generate a signal representative of a position of anchor 14 relative to tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 280 includes an emitter array 304. Emitter array 304 is configured for generating a signal to sensor array 302 of a surgical navigation system 306. In some embodiments, the signal generated by emitter array 304 represents a position of anchor 14 relative to tissue, for example, bone. In some embodiments, the signal generated by emitter array 304 represents a three-dimensional position of anchor 14 relative to tissue.

In some embodiments, sensor array 302 receives signals from emitter array 304 to provide a three-dimensional spatial position and/or a trajectory of anchor 14 relative to tissue. Emitter array 304 communicates with a processor of a computer 308 of surgical navigation system 306 to generate data for display of an image on a monitor 310, as described herein. In some embodiments, sensor array 302 receives signals from emitter array 304 to provide a visual representation of a position of anchor 14 relative to tissue. See, for example, similar surgical navigation components and their use as described in U.S. Pat. Nos. 6,021,343, 6,725,080, and 6,796,988, the entire contents of each of these references being incorporated by reference herein.

Surgical navigation system 306 is configured for acquiring and displaying medical imaging, for example, x-ray images appropriate for a given surgical procedure. In some embodiments, pre-acquired images of a patient are collected. In some embodiments, surgical navigation system 306 can include an O-arm® imaging device 312 sold by Medtronic Navigation, Inc. having a place of business in Louisville, Colo., USA. Imaging device 312 may have a generally annular gantry housing that encloses an image capturing portion 314.

In some embodiments, image capturing portion 314 may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of surgical navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, such as, for example, an optical tracking system that includes an optical localizer, such as, for example, sensor array 302 and/or an EM tracking system that can include an EM localizer. Various tracking devices can be tracked with tracking system 316 and the information can be used by surgical navigation system 306 to allow for a display of a position of an item, such as, for example, a patient tracking device, an imaging device tracking device 320, and an instrument tracking device, such as, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, and 5,592,939, the entire contents of each of these references being incorporated by reference herein.

Fluoroscopic images taken are transmitted to a computer 318 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 100 relative to surgical instrument 12 and/or tissue can be tracked. Sensor array 302 is located in such a manner to provide a clear line of sight with emitter array 304, as described herein. In some embodiments, fiducial markers 322 of emitter array 304 communicate with sensor array 302 via infrared technology. Sensor array 302 is coupled to computer 308, which may be programmed with software modules that analyze signals transmitted by sensor array 302 to determine the position of each object in a detector space.

Surgical instrument 12 is configured for use with a guide member, for example, an end effector 200 of robotic arm R to determine axial trajectory of a surgical pathway and/or facilitate positioning of one or more surgical instruments, implants and/or components of spinal implant system 10 in alignment with the axial trajectory of a surgical pathway. End effector 200 includes an inner surface 202 that defines a cavity, for example, a channel 204. Channel 204 is configured for disposal of one or more components of surgical instrument 12 and/or implants. Robotic arm R includes position sensors (not shown), similar to those referenced herein, which measure, sample, capture and/or identify positional data points of end effector 200 in three-dimensional space for a guide-wireless insertion of surgical instrument 12 with tissue. In some embodiments, the position sensors of robotic arm R are employed in connection with surgical navigation system 306 to measure, sample, capture and/or identify positional data points of end effector 200 in connection with surgical treatment, as described herein. The position sensors are mounted with robotic arm R and calibrated to measure positional data points of end effector 200 in three-dimensional space, which are communicated to computer 308.

Tip 26 is provisionally fixed with bone B1 to define an axial trajectory AT, as shown in FIG. 14. Axial trajectory AT of anchor 14 is confirmed by communication of navigation component 280 with surgical navigation system 306, as described herein.

To dock anchor 14, slider 64 is translated into the retracted position. Translation of slider 64 causes sleeve 66 to simultaneously translate into the retracted position. In the retracted position, sleeve 66 is spaced a distance from collar 282, as shown in FIG. 15, to allow anchor 14 to translate through dilator 30 to extend further from end 34 of dilator 30 to drive anchor 14 a greater depth into bone B1 for docking. Anchor 14 is docked with bone B1 along axial trajectory AT.

Figure 17:
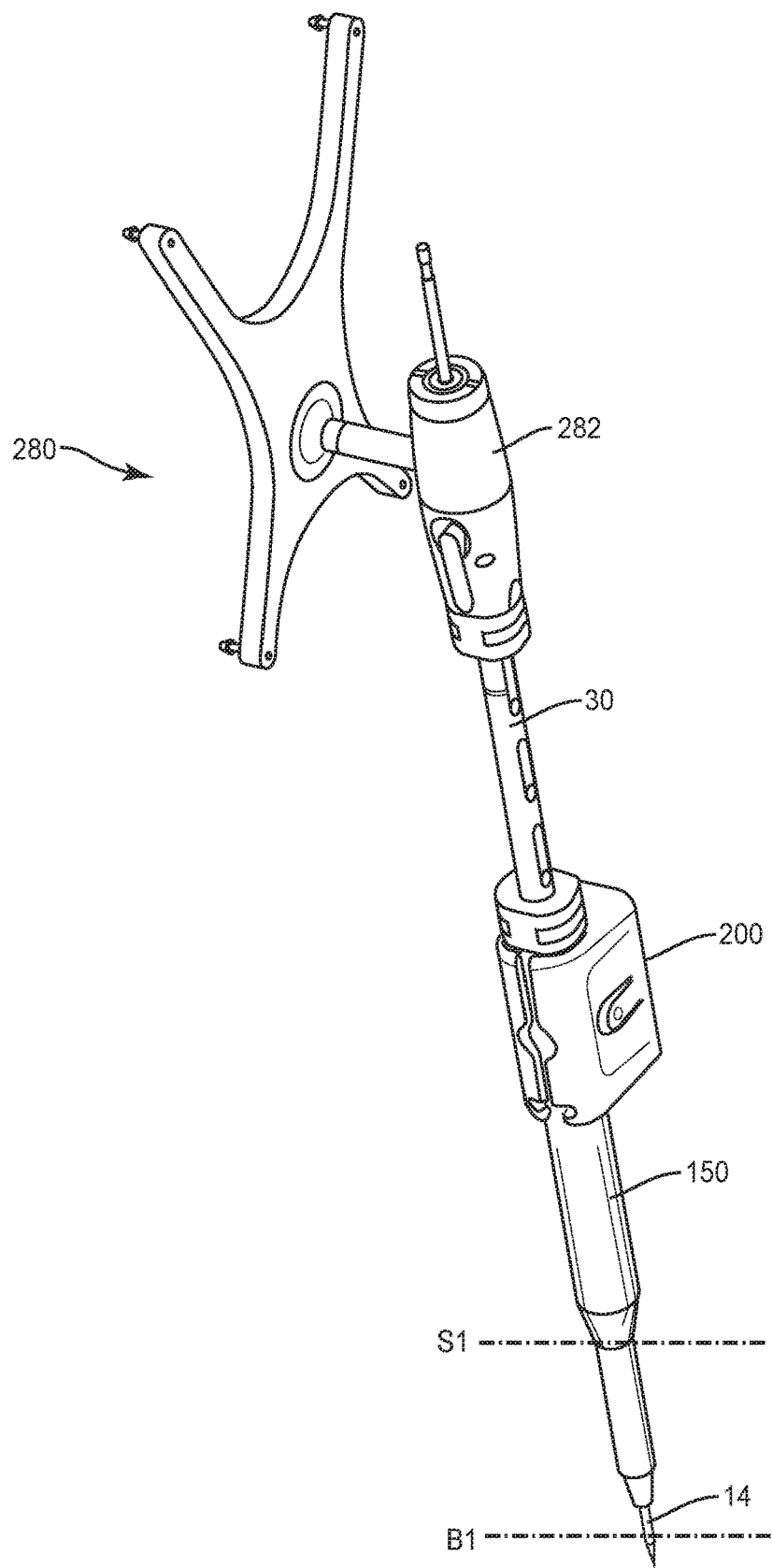
FIG. 17 is a perspective view of components of one embodiment of a surgical system in accordance with the principles of the present disclosure.
Figure 18:
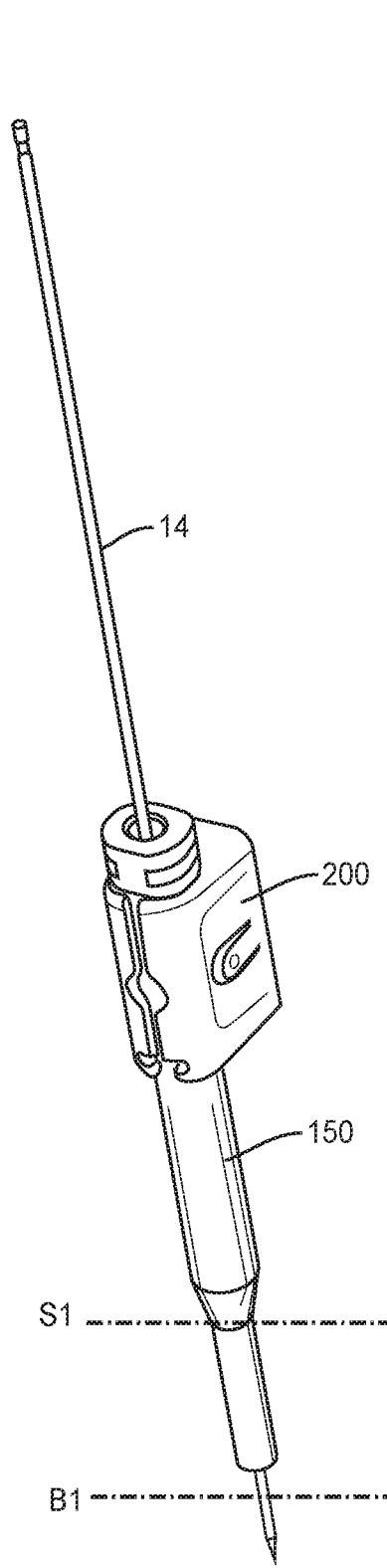
FIG. 18 is a perspective view of components of one embodiment of a surgical system in accordance with the principles of the present disclosure.

Anchor tool 24 is removed from anchor 14, as shown in FIG. 17. To release anchor 14, button 62 is actuated to cause surface 84 to disengage surface 20 of groove 22 to release anchor 14. Opening 86 aligns with channel 74 to allow anchor 14 to translate therethrough for disengagement from anchor tool 24. In some embodiments, slap hammer 94 is utilized to facilitate releasing anchor 14 from bone B1. Dilator 30 is removed from anchor 14, as shown in FIG. 18.

Figure 19:
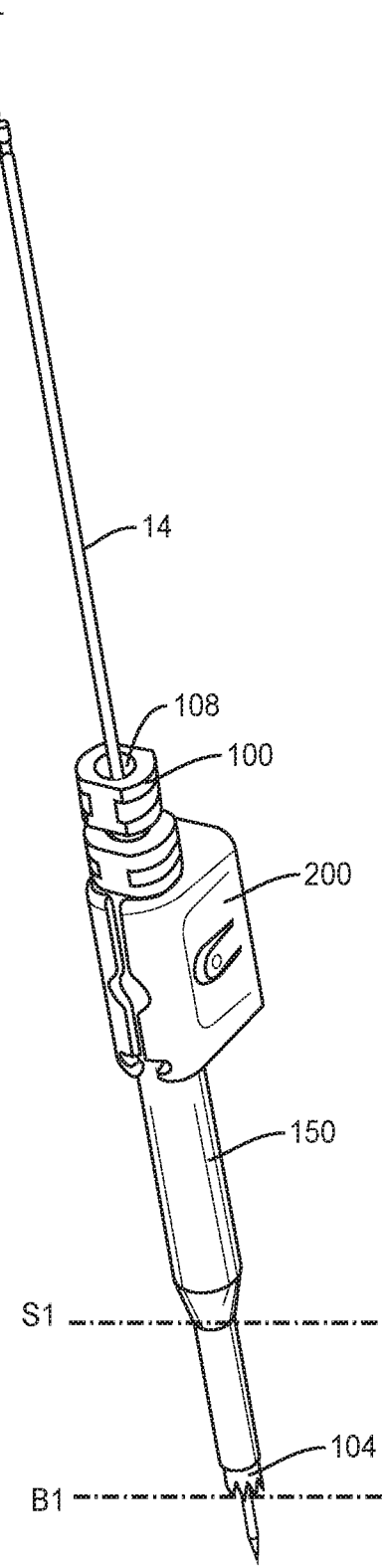
FIG. 19 is a perspective view of components of one embodiment of a surgical system in accordance with the principles of the present disclosure.

Drill guide 100 is mounted with anchor 14, as shown in FIG. 19, such that anchor 14 is disposed with passageway 108. Anchor 14 directs and/or guides drill guide 100 along axial trajectory AT through cannula 150. End 104 of drill guide 100 extends from a distal end of cannula 150. Drill guide 100 is tamped along anchor 14 and axial trajectory AT causing end 104 to engage bone B1. As such, drill guide 100 is docked with bone B1 along navigated axial trajectory AT thereby maintaining the alignment and/or trajectory of drill guide 100 during docking.

Anchor 14 is removed from bone B1 by reattaching anchor tool 24. Anchor 14 is translated into channel 72 and channel 74. Button 62 is actuated causing opening 86 to align with channel 74 to allow anchor 14 to translate therethrough. Button 62 is released and the bias of springs 88 pushes button 62 causing surface 84 to engage surface 20 of groove 22 to capture anchor 14. In some embodiments, slap hammer 94 is utilized to facilitate releasing anchor 14 from bone B1. Anchor 14 is removed from bone B1 and the surgical site.

A drill (not shown) is paired with a selected drill bit and inserted into drill guide 100. Drill guide 100 directs and/or guides the drill along the axial trajectory AT. In some embodiments, the drill includes a navigation component, similar to navigation component 280 as described herein. The navigation component is oriented relative to sensor array 302 to confirm trajectory by communication of the navigation component with surgical navigation system 306, similar to that described herein. Pilot holes (not shown) are made with the selected areas of bone for receiving spinal implants such as bone fasteners for the surgical procedure.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument:
   a first member extending between a proximal end and a distal end configured for fixation with tissue;
   a second member defining a longitudinal passageway and being connected with a navigation component such that the distal end is disposable with the passageway at a selected distance from the navigation component, the navigation component being positioned relative to a sensor to communicate a signal representative of an orientation of the first member;
   a third member extending between a proximal end and a distal end, the third member being mountable with the first member along the orientation such that the distal end of the third member is engageable with the tissue; and
   a fourth member comprising a protrusion, a hole extending through the protrusion and a channel, the hole and the channel each being configured for disposal of the first member, the channel defining a longitudinal axis, the protrusion being movable in a direction that is transverse to the longitudinal axis between a first position in which the hole is offset from the channel and the protrusion blocks the channel and second position in which the hole is aligned with the channel and the protrusion does not block the channel.

2. A surgical instrument as recited in claim 1, wherein the orientation includes an axial trajectory of the first member relative to tissue.

3. A surgical instrument as recited in claim 2, wherein the third member is guided by the first member along the axial trajectory for engagement with tissue.

4. A surgical instrument as recited in claim 1, wherein the second member is removable from the first member such that the third member is mountable with the first member.

5. A surgical instrument as recited in claim 1, wherein the distal end of the first member includes a pointed tip configured to penetrate tissue.

6. A surgical instrument as recited in claim 1, wherein the proximal end of the first member includes a groove.

7. A surgical instrument as recited in claim 1, wherein the second member includes a tapered tip.

8. A surgical instrument as recited in claim 1, wherein the second member includes a cannulated dilator.

9. A surgical instrument as recited in claim 1, wherein the fourth member is configured to adjust a depth of the first member.

10. A surgical instrument as recited in claim 1, wherein the fourth member includes a body that defines the channel, the protrusion being movably disposed in a slot of the body, the hole having a fixed diameter.

11. A surgical instrument as recited in claim 1, wherein the protrusion is biased to the first position by a spring.

12. A surgical instrument as recited in claim 1, wherein the protrusion engages the first member when the protrusion is in the first position.

13. A surgical instrument as recited in claim 1, wherein the proximal end of the first member includes a groove, the protrusion engaging the first member when the protrusion is in the first configuration.

14. A surgical instrument as recited in claim 1, wherein the proximal end of the first member includes a groove, the protrusion engaging the first member when the protrusion is in the first configuration to fix the first member relative to the fourth member.

15. A surgical instrument:
   an anchor extending between a proximal end and a distal end configured for fixation with tissue;
   a dilator defining a longitudinal passageway and being connected with a navigation component such that the distal end is disposable with the passageway at a selected distance from the navigation component, the navigation component being positioned relative to a sensor to communicate a signal representative of an orientation of the anchor;
   a drill guide being mountable with the anchor along the orientation such that a distal end of the drill guide is engageable with the tissue; and
   an anchor tool comprising a protrusion, a hole extending through the protrusion and a channel, the hole having a fixed diameter, the hole and the channel each being configured for disposal of the anchor, the channel defining a longitudinal axis, the protrusion being movable in a direction that is transverse to the longitudinal axis between a first position in which the hole is offset from the channel and the protrusion blocks the channel and second position in which the hole is aligned with the channel and the protrusion does not block the channel.

16. A surgical instrument as recited in claim 15, wherein the orientation includes an axial trajectory of the anchor relative to tissue.

17. A surgical instrument as recited in claim 15, wherein the drill guide is guided by the anchor along the axial trajectory for engagement with tissue.

18. A surgical instrument:
   an anchor configured for fixation with tissue;
   a dilator defining a longitudinal passageway and being connected with a navigation component such that the distal end is disposable with the passageway at a selected distance from the navigation component, the navigation component being positioned relative to a sensor to communicate a signal representative of an orientation of the anchor;

a drill guide being mountable with the anchor along the orientation such that a distal end of the drill guide is engageable with the tissue; and an anchor tool connectable with the anchor and configured to adjust a depth of the anchor relative to tissue and the navigation component, the anchor tool comprising a protrusion, a hole extending through the protrusion and a channel, the hole having a fixed diameter, the hole and the channel each being configured for disposal of the anchor, the channel defining a longitudinal axis, the protrusion being movable in a direction that is transverse to the longitudinal axis between a first position in which the hole is offset from the channel and the protrusion blocks the channel and second position in which the hole is aligned with the channel and the protrusion does not block the channel.

19. A surgical instrument as recited in claim 18, wherein the orientation includes an axial trajectory of the anchor relative to tissue.

20. A surgical instrument as recited in claim 18, wherein the drill guide is guided by the anchor along the axial trajectory for engagement with tissue.

\* \* \* \* \*